(12) United States Patent
Shete et al.

(10) Patent No.: US 10,098,890 B2
(45) Date of Patent: Oct. 16, 2018

(54) STABLE CARFILZOMIB FORMULATIONS

(71) Applicant: Cipla Limited, Mumbai, Maharashtra (IN)

(72) Inventors: Harshad Kishore Shete, Solapur (IN); Pankaj Omprakash Pathak, Thane (IN); Sarabjit Singh, Bangalore (IN); Geena Malhotra, Mumbai (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 15/796,021

(22) Filed: Oct. 27, 2017

(65) Prior Publication Data

US 2018/0117054 A1    May 3, 2018

(30) Foreign Application Priority Data

Oct. 29, 2016  (IN) .............................. 201621037183

(51) Int. Cl.
| | | |
|---|---|---|
| *A61K 38/00* | (2006.01) | |
| *A61K 31/5377* | (2006.01) | |
| *A61K 9/00* | (2006.01) | |
| *A61K 47/18* | (2017.01) | |
| *A61K 47/12* | (2006.01) | |

(52) U.S. Cl.
CPC ........ *A61K 31/5377* (2013.01); *A61K 9/0019* (2013.01); *A61K 38/00* (2013.01); *A61K 47/12* (2013.01); *A61K 47/18* (2013.01)

(58) Field of Classification Search
CPC ....................................................... A61K 38/00
USPC ........................................................ 514/19.2
See application file for complete search history.

(56) References Cited

U.S. PATENT DOCUMENTS

| 7,737,112 B2 | 6/2010 | Lewis et al. |
| 2014/0073558 A1 | 3/2014 | Metcalf et al. |
| 2017/0202901 A1* | 7/2017 | Hippalgaonkar ...... A61K 38/07 |

FOREIGN PATENT DOCUMENTS

WO  2015198257 A1  12/2015

OTHER PUBLICATIONS

Cartilzomib Prescribing Information, dated May 2017, 54 pages.

\* cited by examiner

*Primary Examiner* — Raymond J Henley, III
(74) *Attorney, Agent, or Firm* — Meunier Carlin & Curfman LLC

(57) ABSTRACT

Disclosed herein are stabilized formulations of carfilzomib. The formulations exhibit increased storage stability relative to other formulations, and are simpler for health care providers to prepare and administer to patients.

21 Claims, 1 Drawing Sheet

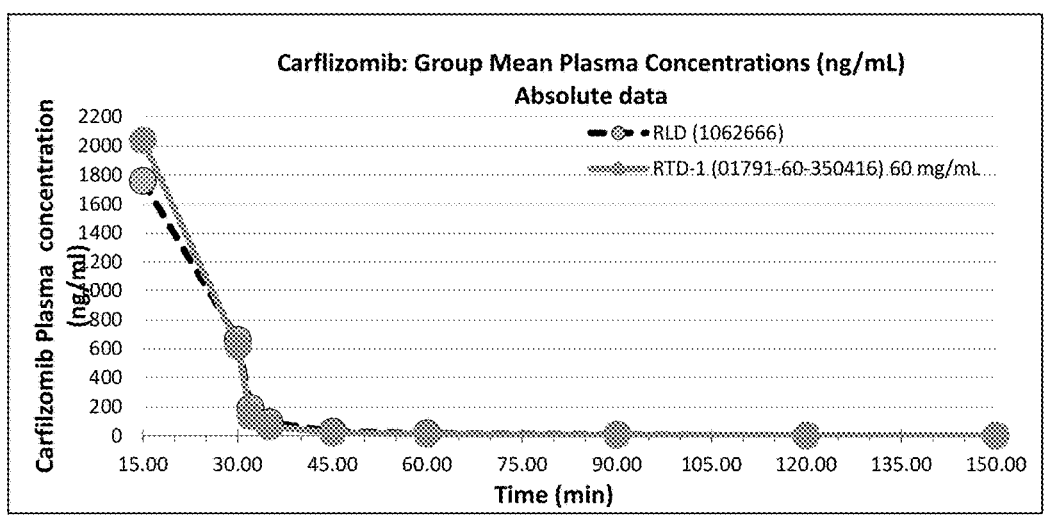

STABLE CARFILZOMIB FORMULATIONS

CROSS REFERENCE TO RELATED APPLICATION

This application claims the benefit of Indian Application 201621037183, filed on Oct. 29, 2016, the contents of which are hereby incorporated in its entirety.

FIELD OF THE INVENTION

The invention is directed to stabilized formulations of carfilzomib and related compounds in the form of ready-to-use and ready-to-dilute solution and concentrates.

BACKGROUND

Carfilzomib is a selective proteasome inhibitor indicated for the treatment of multiple myeloma. Carfilzomib is a tetrapeptide epoxyketone proteasome inhibitor that irreversibly binds to the N-terminal threonine-containing active sites of the 20S proteasome, the proteolytic core particle within the 26S proteasome. Carfilzomib has antiproliferative and proapoptotic activities in vitro in solid and hematologic tumor cells. In animals, carfilzomib inhibited proteasome activity in blood and tissue and delayed tumor growth in models of multiple myeloma, hematologic, and solid tumors.

Carfilzomib is commercially marketed under the name Kyprolis® in single dose vials containing either 30 mg or 60 mg of the active ingredient. Each vial, in addition to lyophilized carfilzomib, also contains sulfobutylether beta-cyclodextrin, citric acid and sodium hydroxide for pH adjustment (target pH 3.5).

The lyophilized products require reconstitution prior to intravenous infusion. The process of reconstitution requires several lengthy and complex steps comprising aseptically reconstituting each vial by slowly injecting sterile water for injection through the stopper, directing the water onto the inside wall of the vial to minimize foaming. After the water is added, the vial is gently swirled and/or slowly inverted for about 1 minute, or until complete dissolution occurs. If foaming occurs, the solution is allowed to settle in the vial until foaming subsides (approximately 5 minutes) and the solution becomes clear. After reconstitution, the vial must be visually inspected, and a dose that appears to have any discoloration or particulate matter must be discarded.

One of the difficulties with the commercially available formulation is that the administration process is complex and involves many steps. As described above, the person administering the drug must first create a solution and then subsequently transfer that premix solution into an infusion bag. As carfilzomib is extremely toxic, strict precautions have to be taken in order to minimize handling hazards involving dilution of injection and subsequent preparation of an infusion solution. In making the premix solution, the medical practitioner is required to manually invert the vial for 1 minute repeatedly to allow for complete dissolution. The prescribing information for KYPROLIS® gives very clear instructions not to shake the vial to avoid foaming or spillage. Foaming may result in potency loss. A further difficulty of the commercialized available product is that the premix solution must be added to the infusion bag soon after making of such an admixture. Further, once added to the infusion bag, the carfilzomib has limited stability. The prescribing information notes that once reconstituted, the carfilzomib solutions are stable for only 24 hours when refrigerated, and only four hours at room temperature.

There have been efforts to obtain improved carfilzomib compositions. For instance, substituted cyclodextrin additives have been explored to enhance the solubility of the active ingredient. However, the high cost and limited accessibility of substituted cyclodextrins limits their use in pharmaceutical compositions As carfilzomib has extremely low aqueous solubility, the development of a stable carfilzomib injection is very challenging. There remains a need for improved formulations of carfilzomib having improved ease of manufacture, means of administration, and stability over time. There remains a need for formulations which are easy for healthcare providers to prepare and administer. There remains a need for carfilzomib formulations having improved stability over time, especially when stored under ambient conditions.

It is an object of the invention to provide stabilized, ready-to-dilute, carfilzomib formulations.

It is another object of the invention to provide stabilized, ready-to-use, carfilzomib formulations.

It is another object of the invention to provide a process for preparing stabilized, ready-to-dilute, carfilzomib formulations.

It is another object of the invention to provide a process for preparing stabilized, ready-to-use, carfilzomib formulations.

It is another object of the present invention to provide safe, efficacious and easy to use formulations of carfilzomib.

It is another object of the present invention to provide methods for treating patients with multiple myeloma by administering stable ready-to-dilute/ready-to-use parenteral formulations of carfilzomib.

SUMMARY

According to some embodiments, the formulation can include protease inhibitor, for instance carfilzomib or a pharmaceutically acceptable salt thereof. In some embodiments, the formulation does not include any cyclodextrin compounds. In some embodiments the formulations are in the form of ready-to-dilute and/or ready-to-use solutions or concentrates.

According to some embodiments, the formulation can be a single dose formulation of carfilzomib in a vial, ready for direct dilution with infusion solution.

According to some embodiments, the formulation can be a carfilzomib ready-to-dilute formulation containing dimethyl acetamide.

According to some embodiments, the formulation can be a single dose formulation of carfilzomib, ready for direct introduction into an infusion bag or direct dilution with infusion solution.

According to some embodiments, the formulation can be a stable ready-to-use formulation of carfilzomib that can be directly administered to patient without first combining with a pharmaceutically acceptable diluent.

In some embodiments, the formulation can be stable ready-to-use or ready-to-dilute formulations of carfilzomib ready for direct administration using a pre-filled syringe.

Also disclosed herein are processes for preparation of ready-to-dilute formulations of carfilzomib and ready-to-use formulations.

Also disclosed herein are method for treating patients with multiple myeloma by administering ready-to-dilute or ready-to-use formulations of carfilzomib. The multiple myeloma can be either relapsed or refractory. The carfilzomib can be administered as either the single agent or as part of a combination therapy, for instance with dexamethasone or lenalidomide plus dexamethasone.

The details of one or more embodiments are set forth in the descriptions below. Other features, objects, and advantages will be apparent from the description and from the claims.

BRIEF DESCRIPTION OF THE FIGURES

FIG. 1 depicts carfilzomib plasma concentration resulting after administration of an embodiment of the invention in comparison with a non-stabilized formulation.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The term "carfilzomib" is used in broad sense to include not only "carfilzomib" per se but also its pharmaceutically acceptable derivatives thereof. Suitable pharmaceutically acceptable derivatives include pharmaceutically acceptable salts, pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, ptoluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

The term "stable formulations" refers to any preparation of carfilzomib having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about 2 years. In some embodiments, a stable formulation is one in which no more than 2% of carfilzomib impurities are formed over the storage period. In some embodiments no more than 1.5% of carfilzomib impurities are formed over the storage period. In some embodiments no more than 1% of carfilzomib impurities are formed over the storage period. In certain embodiments no more than 0.4% of any single carfilzomib impurity is formed over the storage period. In other embodiments no more than 0.2% of any single carfilzomib impurity is formed over the storage period. In certain embodiments, stability may be assessed after storing the formulation in a sealed, sterile container at 60% relative humidity at a temperature of 2-8° C.

As used herein, the term "carfilzomib impurity" refers to any compound resulting from the chemical degradation of carfilzomib. Exemplary degradation pathways include amide and/or epoxide hydrolysis, oxidation, epimerization, and products resulting from oxirane-ring opening with various nucleophiles, e.g., chlorine.

In some embodiments, the ready-to-use and ready-to-dilute formulations are substantially free of water. In some embodiments, the formulations contain no more than 1.5%, no more than 1%, no more than 0.5%, no more than 0.25%, or no more than 0.1% by weight of water. Injectable formulations can be prepared in conventional forms, either as liquid or solutions ready for reconstitution or suspension in a liquid form prior to injection, or as emulsions. Sterile injectable formulations can be prepared according to techniques known in the art using suitable carriers, excipients, dispersing or wetting agents, and suspending agents. The ready-to-dilute formulation may be combined with pharmaceutically acceptable vehicle, e.g., a diluent or solvent. In some embodiments, the ready-to-dilute formulations are combined with water for injection, isotonic dextrose solution, Ringer's solution, isotonic sodium chloride solution, and suitable non-aqueous solvents safe for parenteral administration. In addition, sterile fixed oils, fatty esters, or polyols are conventionally employed as solvents or suspending media.

The disclosed formulations of the present application are particularly suited for injection, but it will be understood that the solutions may have alternative uses. Injectable formulations may be administered via any route including intramuscular, intravenous, or subcutaneous.

The formulations can be in the form of liquid concentrates, ready-to-dilute and/or ready-to-use solutions. The ready-to-dilute and ready-to-use formulations may be packaged within a conventional sterile vial or other container. Alternatively, the formulations may be packaged in a sterile syringe already fitted with a needle for injection.

The term "ready-to-dilute" refers to a formulation which can be directly combined with a diluent (e.g., dextrose solution, saline solution, or any other infusion medium) and then administered to a patient. In some embodiments, the ready-to-dilute formulation may be provided as a single vial containing the carfilzomib formulation. In other embodiments, the ready-to-dilute formulation may be accompanied by a pharmaceutically acceptable diluent in a separate container (i.e., a dual vial formulation).

The term "ready-to-use" refers to any preparation of carfilzomib which can be administered to patient directly without any further dilution or processing.

The liquid formulations can contain carfilzomib at concentrations from about 5 mg/mL to about 200 mg/mL. In embodiments, the concentrations of carfilzomib are in the range from about 10 mg/mL to about 60 mg/mL, or about 15 mg/mL to about 50 mg/mL, or about 30 mg/mL to about 60 mg/mL. Especially preferred embodiments include those having carfilzomib at a concentration of about 30 mg/mL or about 60 mg/mL.

In some embodiments, the application provides a pharmaceutical composition comprising carfilzomib, a solvent system comprising one or more pharmaceutically acceptable, water miscible organic solvent suitable for injection and an acid stabilizer.

The persons skilled in the art will understand that when the solvent system is described as non-aqueous, this indicates that water is not present in appreciable amounts in the solvent system nor is water specifically added to the composition. However, there can be some trace amount of water present in the composition due to its presence in some of the commercial components used (e.g., surfactants), and water may also be absorbed from the environment into the composition. Compositions containing such incidental or trace amount of water are included within the scope of the application. In some embodiments, the total water contents is less than about 2% by weight, less than about 1.5% by weight, less than 1.0% by weight, less than 0.5% by weight, less than 0.25% by weight, or less than 0.1% by weight. Water content may be measured using Karl-Fischer titration methods.

In embodiments, the pharmaceutically acceptable non-aqueous solvent system may comprise at least one pharmaceutically acceptable, water miscible organic solvents. In some embodiments, the ready-to-use and ready-to-dilute compositions can include ethanol, isopropyl alcohol, benzyl alcohol, propylene glycol, polyethylene glycol, glycerol, dimethylacetamide, N-methylpyrrolidone, dimethylsulfoxide (DMSO), diethylene glycol monoethyl ethers, caprylocaproyl polyoxyl-8 glycerides, glycofurol, or mixtures thereof.

In some embodiments the formulations can be prepared using dimethylacetamide, for instance substantially anhydrous dimethylacetamide having a water content of not more than 2%. In other embodiments the substantially anhydrous dimethylacetamide can have a water content of not more than 1%. In other embodiments the substantially anhydrous dimethylacetamide can have a water content of not more than 0.1%. The skilled person will recognize that the lower the water content of the solvent used to prepare the formulation, the lower the water content of the formulation will be.

The ready-to-use and ready-to-dilute formulations may include one or more acid stabilizers. In certain embodiments, the acid stabilizer than be a $C_{1-6}$alkyl carboxylic acid, for instance formic acid, acetic acid, 1-propionic acid, 2-propionic acid, n-butyric acid, t-butyric acid, isobutyric acid, or sec-butyric acid. In some embodiments the acid stabilizer than by a hydroxy substituted-carboxylic acid or polycarboxylic acid, e.g., a compound having two or more carboxylic acid functional groups. Such compounds include, for instance, lactic acid, glycolic acid, 3-hydroxypropionic acid, hydroxylbutyric acid, malonic acid, succinic acid, malic acid, tartaric acid, citric acid, fumaric acid, muramic acid, gluconic acid and glucuronic acid. The skilled person will recognize that in order to obtain a substantially water free formulation, the acid stabilizer should be substantially free of water prior to its use in the formulation. When the acid stabilizer compound is a solid a room temperature, it can be a substantially anhydrous crystalline solid, for instance, having a water content no greater than 5% by weight, no greater than 4% by weight, no greater than 3% by weight, no greater than 2% by weight, no greater than 1% by weight, no greater than 0.5% by weight, no greater than 0.25% by weight, or no greater than 0.1% by weight.

The acid stabilizer may be present in an amount in the range from about 1 to about 500 mg/mL, from about 10 to about 400 mg/mL, 20 to about 300 mg/mL, from about 30 to about 300 mg/mL, from about 100 to about 300 mg/mL, from about 150 to about 300 mg/mL, from about 180 to about 300 mg/mL, or from about 200 to about 300 mg/mL.

The pharmaceutical compositions of the invention may optionally comprise one or more pharmaceutically acceptable excipients, such as a buffer, surfactant, antioxidant, preservative, and/or isotonicity agent. The use of said pharmaceutically acceptable excipients in appropriate amounts or quantity can be readily determined by any person with ordinary skill in the art.

In some embodiments, the ready-to-use and ready-to-dilute formulations can include one or more pharmaceutically acceptable solubilizers. Solubility enhancement with the incorporation of solubilizer may involve micellar solubilization, co-solvency, complexation, prodrug formation, or salt formation.

Generally, the formulations disclosed herein will not contain any cyclodextrin compounds. As used herein, the term "cyclodextrin" refers to any cyclic compound composed of multiple carbohydrate (e.g., glucopyranoside) units. Carfilzomib in formulations disclosed herein has substantially the same solubility and pharmacokinetic behavior as carfilzomib complexed with cyclodextrin.

The formulation can include one or more pharmaceutically acceptable surfactants. Suitable surfactants include anionic, cationic, amphoteric and non-ionic surfactants, Exemplary non-ionic surfactants include polyethylene oxides, for instance PEG 300 or PEG 400. Pharmaceutically acceptable surfactant for this application include, but are not limited to, polysorbate or polyethoxylated castor oil, Polyoxyl 20 stearate, Polyoxyl 35 castor oil, poloxamer, polyoxyethylene sorbitan monoisostearate, polyethylene glycol 40 sorbitan diisostearate, Polyoxyl 40 Hydrogenated castor oil, Polysorbate, Polysorbate 20, Polysorbate 40, Polyoxyl 60 stearate, Polysorbate 85, Polysorbate 60, poloxamer 331, polyoxyethylene fatty acid esters, Polyoxyl 40 castor oil, poloxamer 188, polyoxyethylene polyoxypropylene 1800, oleic acid, Sodium desoxycholate, Sodium lauryl sulfate, Sorbitan monolaurate, Sorbitan monooleate, Sorbitan monopalmitate, Sorbitan trioleate, N-Carbamoyl methoxypolyethylene glycol 2000-1,2-distearol, myristic acid, Steareth, Stearic acid, Polyoxyl 40 stearate, Sucrose stearate, Tocopherol, polyoxyl castor oil, Triglyceride synthetic, Trimyristin, Tristearin, magnesium stearate, lecithin, lauryl sulfate, Vitamin E, egg yolk phosphatides, docusate sodium, Polysorbate 80, dimyristoyl phosphatidylglycerol, dimyristoyl lecithin, Capryol 90 (propylene glycol monocaprylate), Capryol PGMC (propylene glycol monocaprylate), deoxycholate, cholesterol, Cremophor EL, Propylene glycol alginate, Croval A-10 (PEG 60 almond glycerides), Labrafil 1944 (oleoyl macrogol-6 glycerides), Labrafil 2125 (linoleoyl macrogol-6 glycerides), Labrasol (caprylocaproyl macrogol-8 glycerides), Lauroglycol 90 (propylene glycol monolaurate), Lauroglycol FCC (propylene glycol laurate), calcium stearate, Lecithin Centromix E, Lecithin Centrophase 152, Lecithin Centrol 3F21B, POE 26 glycerin, Olepal isoteariques (PEG-6 isostearate), Plurol diisostearique (polyglycerol-3-diisostearate), Plurol Oleique CC, POE 20 Sorbitan trioleate, Tagat TO (polyoxyethylene glycerol trioleate), or Solutol (macrogol-15 hydroxystearate). In some embodiments, the surfactant can be present in an about 10% to about 90% of the total weight of the ready-to-dilute formulation, preferably from about 30% to about 60% of the total weight of the ready-to-dilute formulation.

While not wishing to be bound by any theory, it is believed that the use of anhydrous excipients such as acid stabilizers, organic solvents, buffers, antioxidants, surfactants, preservatives and isotonicity agents in preparing carfilzomib compositions of the invention play a significant role in reducing the degradation of carfilzomib thereby prolonging the shelf-life of said carfilzomib compositions. It is also believed that the epoxy ketone moiety present in carfilzomib undergoes hydrolysis and leads to formation of several impurities. Substantial exclusion of water during the processing steps and use of excipients which are substantially free from water are thus preferred for obtaining stable carfilzomib compositions of the invention.

Certain compounds have been identified as impurities stemming from carfilzomib degradation:

| Carfilzomib impurities | Name (IUPAC) |
|---|---|
| Acid impurity | (S)-2-((S)-4-methyl-2-((S)-2-(2-morpholinoacetamido)-4-Phenyl butanamido)pentanamido)-3-phenylpropanoic acid |
| Diol Impurity | (S)-N-((S)-1-(((2R,4S)-1,2-dihydroxy-2,6-dimethyl-3-oxoheptan-4-yl)amino)-1-oxo-3-phenylpropan-2-yl)-4-methyl-4-methyl-2-((S)-2-(2-morpholinoacetamido)-4-phenylbutanamido)pentanamide |

-continued

| Carfilzomib impurities | Name (IUPAC) |
|---|---|
| N-Oxide impurity | 4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholine-4-oxide |
| Chloro impurity | (S)-N-((S)-1-(((2S,4S)-1-chloro-2-hydroxy-2,6-dimethyl-3-oxoheptan-4-yl)amino)-1-oxo-3-phenylpropan-2-yl)-4-methyl-2-((S)-2-(2-morpholinoacetamido)-4-phenylbutanamido)pentanamide |
| Diastereomer impurity | (S)-4-methyl-N-((R)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide |

In some embodiments, after storage for six months at 60% RH and at a temperature between about 2-8° C., the carfilzomib compositions can have no more than 0.4% of the acid impurity by HPLC. Likewise, in some embodiments, the carfilzomib compositions can have no more than 0.4% of the diol impurity by HPLC. In some embodiments, the composition can contain no more than 1.0% total carfilzomib impurity by HPLC. In some embodiments, the composition can contain no more than 0.5% of any single carfilzomib impurity, by HPLC. In some embodiments, the composition can contain no more than 0.1% of any single carfilzomib impurity, by HPLC.

A person skilled in the art will be aware that pH is a measure of free hydrogen ions in a solution. For example, free hydrogen ions will exist in organic solvents systems that may contain acids. The pH may be measured by placing a pH meter electrode directly into liquid formulations, such pH meter having been calibrated for the appropriate pH range with standard aqueous buffers. Persons skilled in the art will know of other methods which may be used to measure pH. Such persons will further know that, while the pH meter reading obtained for a substantially non-aqueous formulation may not be a true reflection of the actual hydrogen ion concentration in the solution, it may nonetheless give a meaningful and reproducible measurement that indicates the relative acidity/basicity of the solution, as is the case for the carfilzomib formulations disclosed herein. In instances, the pH meter reading will be in the range from about 3 to 9, or from about 3 to 6, or from about 4 to 6. These ranges are for measurements made at room temperature (20-25° C.).

The addition of the components of the single-vial and dual-vial injection concentrates can be achieved by methods known in the art. For example, one or more of the components may be added to each other and then into a common receptacle for mixing, or the components may be added to a common receptacle in a particular order, or the components may be added to a common receptacle simultaneously. In certain embodiments, the carfilzomib, or other lipophilic molecule, and the solubilizer are combined separately from the other components. In some embodiments, the carfilzomib, or other lipophilic molecule is dissolved in the solubilizer separately from the other components.

The components of the single-vial and dual-vial injection concentrates may be mixed by methods known in the art. For example, the components can be mixed by simple mixing, or may be mixed with a mixing device continuously, periodically, or a combination thereof. Mixing devices may include, but are not limited to, a magnetic stirrer, shaker, a paddle mixer, homogenizer, and any combination thereof.

The addition and mixing of one or more components of the single-vial and dual-vial injection concentrates may occur under controlled conditions. For example, the addition and mixing of the components may occur under conditions such as under nitrogen or at a particular humidity, etc., or the adding and mixing may occur under certain temperatures. In certain embodiments, the adding and mixing may occur under temperature conditions of about 25° C. to about 80° C.

Additionally, the addition and mixing may be under controlled light exposure, such as in yellow light or under protection from direct exposure to light. After the injection concentrate is prepared, it may be sterilized by methods known in the art. The injection concentrate may undergo aseptic filtration (e.g., using a 0.2 µm disposable pre-sterilized membrane filter). Additionally, the injection concentrate may be placed into a container (e.g., an intravenous solution bag, bottle, vial, ampoule, or pre-filled sterile syringe). The container may have a sterile access port for piercing by a hypodermic injection needle. In some embodiments, the injection concentrate may be filled in one or more pre-sterilized depyrogeneated vials and stopped aseptically with a pre-sterilized butyl stopper. In some embodiments, the injection concentrate may be filled in sterile syringe.

The diluted injection concentrate may be formed by mixing the dual-vial injection concentrate and diluent together. In one embodiment the dual-vial injection concentrate may be added to the diluent. In another embodiment, the diluent may be added to the dual-vial injection concentrate. In yet another embodiment, the dual-vial injection concentrate and diluent may be combined together in a pre-sterilized vessel. The dual-vial injection concentrate and diluent may be mixed by repeated inversions, swirling, or other techniques known in the art.

The final dilution for infusion may be prepared by combining a single-vial injection concentrate or a diluted injection concentrate with an infusion solution of the present invention, according to methods known in the art. For example, the single-vial injection concentrate or a diluted injection concentrate may be mixed with an infusion solution in a common receptacle, or the single-vial injection concentrate or the diluted injection concentrate may be injected into an infusion bag containing the infusion solution.

An embodiment of present invention is directed to delivery of carfilzomib, once diluted to appropriate injection (especially infusion, most particularly IV infusion) concentrations, it may be administered in appropriate amounts for treating carfilzomib responsive conditions known in the art.

An embodiment of the present invention, is provided a method for treating patients with relapsed or refractory multiple myeloma by administering stable ready-to-dilute or ready-to-use parenteral formulation of carfilzomib either alone or in combination with dexamethasone or lenalidomide plus dexamethasone.

EXAMPLE

The following examples are for the purpose of illustration of the invention only and are not intended to limit the scope of the present invention in any manner whatsoever.

Example 1—Stabilized Formulations

| Composition | Concentration per vial basis (mg/ml) |
| --- | --- |
| Carfilzomib | 60 mg |
| Lactic acid (anhydrous) | 333 mg |
| Dimethylacetamide (Water content: NMT 0.1%) | 607 µl |
| Total vial volume | q.s. to 1.0 ml |

Lactic acid crystals (anhydrous) were added to anhydrous dimethyl acetamide under stirring at refrigerated conditions (2-8° C.) and under continuous nitrogen sparging. Weighed quantity of carfilzomib was added to above solution under stirring at refrigerated conditions (2-8° C.) and under continuous nitrogen sparging. The solution was then filtered through 0.22 micron filter (PTFE). The obtained sterile solution is then filled in vials, sealed and labelled.

The following Examples (2-14) were also prepared in a manner similar to that described for Example 1 above:

Example 2

| Composition | Concentration per vial basis (mg/ml) |
| --- | --- |
| Carfilzomib | 60 mg |
| Malic acid | 200 mg |
| Dimethylacetamide | 740 µl |
| Total vial volume | q.s. to 1.0 ml |

Example 3

| Composition | Concentration per vial basis (mg/ml) |
| --- | --- |
| Carfilzomib | 60 mg |
| Tartaric acid | 200 mg |
| Dimethylacetamide | 740 µl |
| Total vial volume | q.s. to 1.0 ml |

Example 4

| Composition | Concentration per vial basis (mg/ml) |
| --- | --- |
| Carfilzomib | 60 mg |
| Tartaric acid | 200 mg |
| Labrasol | 870 µl |
| Transcutol HP | 870 µl |
| Total vial volume | q.s. to 2.0 ml |

Example 5

| Composition | Concentration per vial basis (mg/ml) |
| --- | --- |
| Carfilzomib | 60 mg |
| Malic acid | 200 mg |
| Labrasol | 870 µl |
| Transcutol HP | 870 µl |
| Total vial volume | q.s. to 2.0 ml |

Example 6

| Composition | Concentration per vial basis (mg/ml) |
|---|---|
| Carfilzomib | 60 mg |
| Lactic acid (anhydrous) | 200 mg |
| Labrasol | 870 µl |
| Transcutol HP | 870 µl |
| Total vial volume | q.s. to 2.0 ml |

Example 7

| Composition | Concentration per vial basis (mg/ml) |
|---|---|
| Carfilzomib | 60 mg |
| Malic acid | 200 mg |
| N-methylpyrollidone | 740 µl |
| Total vial volume | q.s. to 1.0 ml |

Example 8

| Composition | Concentration per vial basis (mg/ml) |
|---|---|
| Carfilzomib | 60 mg |
| Tartaric acid | 200 mg |
| N-methylpyrollidone | q.s. to 740 µl |
| Total vial volume | 1.0 ml |

Example 9

| Composition | Concentration per vial basis (mg/ml) |
|---|---|
| Carfilzomib | 60 mg |
| Malic acid | 200 mg |
| Benzyl alcohol | 740 µl |
| Total vial volume | q.s. to 1.0 ml |

Example 10

| Composition | Concentration per vial basis (mg/ml) |
|---|---|
| Carfilzomib | 60 mg |
| Tartaric acid | 200 mg |
| Benzyl alcohol | 740 µl |
| Total vial volume | q.s. to 1.0 ml |

Example 11

| Composition | Concentration per vial basis (mg/ml) |
|---|---|
| Carfilzomib | 60 mg |
| Tartaric acid | 200 mg |
| Ethanol | 740 µl |
| Total vial volume | q.s. to 1.0 ml |

Example 12

| Composition | Concentration per vial basis (mg/ml) |
|---|---|
| Carfilzomib | 60 mg |
| Malic acid | 200 mg |
| Ethanol | 740 µl |
| Total vial volume | q.s. to 1.0 ml |

Example 13

| Composition | Concentration per vial basis (mg/ml) |
|---|---|
| Carfilzomib | 60 mg |
| Lactic acid (anhydrous) | 200 mg |
| Dimethylacetamide (Water content: NMT 0.1%) | 607 µl |
| Total vial volume | q.s. to 1.0 ml |

Example 14

| Composition | Concentration per vial basis (mg/ml) |
|---|---|
| Carfilzomib | 60 mg |
| Lactic acid (anhydrous) | 160 mg |
| Dimethylacetamide (Water content: NMT 0.1%) | 840 µl |
| Total vial volume | q.s. to 1.0 ml |

Example A (Comparative)

| Composition | Concentration per vial basis (mg/ml) |
|---|---|
| Carfilzomib | 60 mg |
| Lactic acid | 333 mg |
| Dimethylacetamide | 667 µl |
| Total vial volume | q.s. to 1.0 ml |

Lactic acid was added to dimethyl acetamide under stirring at refrigerated conditions (2-8° C.) and under continuous Nitrogen sparging. Weighed quantity of carfilzomib was added to above solution under stirring at refrigerated conditions (2-8° C.) and under continuous nitrogen sparging. The solution was then filtered through 0.22 micron filter (PTFE) to obtain the final composition.

Example 15—Stability Comparison

The stability Example 13 and 14 above was compared with Comparative Example A. The conditions and the total impurities formed in both the compositions at the end of six months are described in Tables 1A, 1B, and 1C. Formulations prepared according to the disclosed invention exhibited substantially reduced rates of degradation:

TABLE 1A

Description
(Example A)
Batch No. 01791-60-171115 (2-8° C. 60% RH)

| Condition | 1 M | 2 M | 3 M | 6 M | 12 M |
|---|---|---|---|---|---|
| Water Content | | | 5.15 | | |
| Assay | 100 | 101.4 | 99.1 | 97.6 | 95.1 |
| Related Substance (%) | — | — | — | — | — |
| Acid Imp. | ND | ND | 0.11 | 0.20 | 0.10 |
| N-Oxide Imp. | <0.1 | <0.1 | <0.1 | <0.1 | 0.20 |
| Diol Imp (RRT 0.60) | 0.04 | 0.10 | 0.10 | 0.22 | 0.39 |
| Chloro Imp. | — | — | — | <0.1 | <0.1 |
| Imp. at RRT 0.56 | ND | <0.1 | <0.1 | <0.1 | 0.20 |
| Imp. at RRT 0.65 | 0.11 | <0.1 | <0.1 | 0.39 | <0.1 |
| Single Maximum Impurity | 0.19 (RRT 0.69) | 0.41 (RRT 0.69) | 0.50 (RRT 0.69) | 0.82 (RRT 0.67) | 1.33 (RRT 0.69) |
| Total IMP. | 0.30 | 1.17 | 1.57 | 3.29 | 5.48 |

TABLE 1B

Description
(Example 13)
Batch No. 1791-060-350416 (2-8° C. 60% RH)

| Condition | 1 M | 2 M | 3 M | 6 M | 9 M | 12 M |
|---|---|---|---|---|---|---|
| Water Content | | | 0.92 | | | |
| Assay | 99.3 | 99.3 | 99.2 | 95.6 | 98.3 | 98.4 |
| Related Substance (%) | — | — | — | — | — | — |
| Acid Imp. | ND | ND | ND | ND | <0.1 | <0.1 |
| N-Oxide Imp. | <0.1 | <0.1 | <0.1 | <0.1 | <0.1 | <0.1 |
| Diol Imp (RRT 0.60) | <0.1 | ND | <0.1 | <0.1 | <0.1 | <0.1 |
| Chloro Imp. | — | ND | <0.1 | ND | <0.1 | ND |
| Imp. at RRT 0.56 | <0.1 | ND | <0.1 | <0.1 | <0.1 | <0.1 |
| Imp. at RRT 0.65 | <0.1 | <0.1 | <0.1 | ND | <0.1 | <0.1 |
| Single Maximum Impurity | 0.10 (RRT 0.69) | 0.14 (RRT 0.67) | 0.24 (RRT 0.67) | 0.34 (RRT 0.67) | 0.58 (RRT 0.69) | 0.70 (RRT 0.68) |
| Total IMP. | 0.10 | 0.14 | 0.34 | 0.62 | 1.18 | 1.55 |

TABLE 1C

Description
(Example 14)
Batch No. 01791-60-280216 (2-8° C. 60% RH)

| Condition | 1 M | 3 M | 6 M | 12 M |
|---|---|---|---|---|
| Water Content | | 1.19 | | |
| Assay | 102.9 | 101.0 | 98.8 | 96.9 |
| Related Substance (%) | — | — | — | — |
| Acid Imp. | ND | ND | ND | <0.1 |
| N-Oxide Imp. | <0.1 | <0.1 | <0.1 | 0.13 |
| Diol Imp (RRT 0.60). | <0.1 | <0.1 | ND | <0.1 |
| Chloro Imp. | — | — | — | — |
| Imp at RRT 0.56. | ND | <0.1 | <0.1 | <0.1 |
| Imp at RRT 0.65. | <0.1 | <0.1 | <0.1 | ND |
| Single Maximum Impurity | <0.1 | 0.13 (RRT 0.69) | 0.13 (RRT 0.69) | 0.47 (RRT 0.66) |
| Total IMP. | <0.1 | 0.13 | 0.39 | 1.00 |

Example 16—Pharmacokinetic Comparison

Pharmacokinetics of carfilzomib composition prepared in example 1 above was compared with that of commercialized drug product KYPROLIS® marketed by Amgen/Onyx in USA. The single dose comparative intravenous slow Infusion (1 Hour) Pharmacokinetic Study of Carfilzomib was conducted in male-Wistar rats. The results of the study are described in Table 2, Table 3 and in FIG. 1:

TABLE 2

Carfilzomib: Group Mean Plasma Concentrations (ng/mL)

| Time | KYPROLIS ® | Example 13 |
|---|---|---|
| 0 | 0 | 0 |
| 15 | 1760.00 | 2040.00 |
| 30 | 662.00 | 618.00 |
| 32 | 194.00 | 135.00 |
| 35 | 95.60 | 65.10 |
| 45 | 31.10 | 22.90 |
| 60 | 19.10 | 12.30 |
| 90 | 8.66 | 6.39 |
| 120 | 3.93 | 4.11 |
| 150 | 2.30 | 2.14 |

TABLE 3

| PK Parameters | KYPROLIS ® | Example 13 |
|---|---|---|
| $AUC_{0-t}$ (h*ng/mL) | 571 | 624 |
| $AUC_{0-\infty}$ (h*ng/mL) | 573 | 627 |
| $C_{max}$ (ng/mL) | 1760 | 2040 |
| $T_{max\ (minutes)}$ - Median | 15.0 | 15.0 |
| Clearance (mL/min/kg) | 236 | 221 |

TABLE 3-continued

| PK Parameters | KYPROLIS ® | Example 13 |
|---|---|---|
| $V_{ss}$ (L/kg) | 1.26 | 1.01 |
| $T_{1/2}$ (minutes) | 29.8 | 34.9 |

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A liquid ready-to-use or ready-to-dilute composition, comprising carfilzomib or a pharmaceutically acceptable salt thereof, an organic solvent, and an acid stabilizer, wherein the composition, when stored for six months in a sealed, sterile vial at 60% RH at a temperature from 2-8° C., contains no more than 1.0% total impurity, as measured by HPLC, wherein the composition contains no more than 1.5% by weight of water.

2. The composition according to claim 1, wherein the acid stabilizer comprises one or more of a hydroxycarboxylic acid, a polycarboxylic acid, or a mixture thereof.

3. The composition according to claim 2, wherein the acid stabilizer comprises lactic acid, glycolic acid, 3-hydroxypropionic acid, 2-hydroxypropionic acid, 4-hydroxybutyric acid, 3-hydroxybutyric acid, 2-hydroxybutyric acid, malonic acid, succinic acid, malic acid, tartaric acid, citric acid, fumaric acid, muramic acid, gluconic acid, glucuronic acid, or a mixture thereof.

4. The composition according to claim 3, wherein the acid stabilizer is present in an amount from 150-500 mg/mL.

5. The composition according to claim 1, wherein the acid stabilizer is anhydrous lactic acid.

6. The composition according to claim 1, wherein the organic solvent comprises ethanol, isopropyl alcohol, benzyl alcohol, propylene glycol, polyethylene glycol, glycerol, dimethylacetamide, N-methylpyrrolidone, dimethylsulfoxide, diethylene glycol monoethyl ethers, caprylocaproyl polyoxyl-8 glycerides, glycofurol, or a mixture thereof.

7. The composition according to claim 6, wherein the organic solvent comprises dimethylacetamide.

8. The composition according to claim 1, wherein the composition does not contain any cyclodextrin.

9. A method of treating multiple myeloma, comprising administering to a patient in need thereof a liquid ready-to-use or ready-to-dilute composition, comprising carfilzomib or a pharmaceutically acceptable salt thereof, an organic solvent, and an acid stabilizer, wherein the composition, when stored for six months in a sealed, sterile vial at 60% RH at a temperature from 2-8° C., contains no more than 1.0% total impurity, as measured by HPLC, wherein the composition contains no more than 1.5% by weight of water.

10. The method according to claim 9, wherein the composition is ready-to-use and is directly injected into the patient.

11. The method according to claim 9, wherein the composition is ready-to-dilute, and the composition is first combined with a pharmaceutically acceptable diluent prior to administering to the patient.

12. The method according to claim 9, wherein the acid stabilizer comprises one or more of a hydroxycarboxylic acid, a polycarboxylic acid, or a mixture thereof.

13. The method according to claim 9, wherein the acid stabilizer comprises lactic acid, glycolic acid, 3-hydroxypropionic acid, 2-hydroxypropionic acid, 4-hydroxybutyric acid, 3-hydroxybutyric acid, 2-hydroxybutyric acid, malonic acid, succinic acid, malic acid, tartaric acid, citric acid, fumaric acid, muramic acid, gluconic acid, glucuronic acid, or a mixture thereof.

14. The method according to claim 9, wherein the acid stabilizer is present in an amount from 150-500 mg/mL.

15. The method according to claim 9, wherein the acid stabilizer comprises anhydrous lactic acid.

16. The method according to claim 9, wherein the organic solvent comprises ethanol, isopropyl alcohol, benzyl alcohol, propylene glycol, polyethylene glycol, glycerol, dimethylacetamide, N-methylpyrrolidone, dimethylsulfoxide, diethylene glycol monoethyl ethers, caprylocaproyl polyoxyl-8 glycerides, glycofurol, or a mixture thereof.

17. The method according to claim 9, wherein the organic solvent comprises dimethylacetamide.

18. The method according to claim 9, wherein the composition does not contain any cyclodextrin.

19. A process for preparing a liquid ready-to-use or ready-to-dilute carfilzomib composition, comprising preparing a mixture comprising carfilzomib, acid stabilizer and organic solvent, and placing the mixture in a sterilized container, wherein prior to combining the acid stabilizer and organic solvent, the sum total of water in the acid stabilizer and organic solvent is less than 1.5% by weight relative to the total weight of the acid stabilizer and organic solvent.

20. The process according to claim 19, wherein the acid stabilizer comprises lactic acid, glycolic acid, 3-hydroxypropionic acid, 2-hydroxypropionic acid, 4-hydroxybutyric acid, 3-hydroxybutyric acid, 2-hydroxybutyric acid, malonic acid, succinic acid, malic acid, tartaric acid, citric acid, fumaric acid, muramic acid, gluconic acid, glucuronic acid, or a mixture thereof.

21. The process according to claim 19, wherein the acid stabilizer is crystalline, anhydrous lactic acid.

\* \* \* \* \*